United States Patent
Maxwell et al.

(10) Patent No.: US 7,169,548 B2
(45) Date of Patent: Jan. 30, 2007

(54) SPERM CELL PROCESSING AND PRESERVATION SYSTEMS

(75) Inventors: William Maxwell Chisholm Maxwell, Beecroft (AU); Fiona Kate Hollinshead, Paddington (AU); Justine Kellie O'Brien, Paddington (AU); Gareth Evans, Lane Cove (AU)

(73) Assignee: XY, Inc., Fort Collins, CO (US)

( * ) Notice: Subject to any disclaimer, the term of this patent is extended or adjusted under 35 U.S.C. 154(b) by 110 days.

(21) Appl. No.: 10/340,881

(22) Filed: Jan. 9, 2003

(65) Prior Publication Data

US 2004/0055030 A1    Mar. 18, 2004

Related U.S. Application Data

(60) Provisional application No. 60/410,884, filed on Sep. 13, 2002.

(51) Int. Cl.
*A01N 1/02* (2006.01)
(52) U.S. Cl. .......................... 435/2; 435/325
(58) Field of Classification Search ............... 435/2
See application file for complete search history.

(56) References Cited

U.S. PATENT DOCUMENTS

| | | |
|---|---|---|
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp .... 195/1.3 |
| 3,710,933 A | 1/1973 | Fulwyler et al. |
| 3,761,941 A | 9/1973 | Robertson |
| 3,810,010 A | 5/1974 | Thom |
| 3,826,364 A | 7/1974 | Bonner et al. |
| 3,829,216 A | 8/1974 | Persidsky ..................... 356/36 |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton ................. 128/1 R |
| 3,909,744 A | 9/1975 | Wisner et al. |
| 3,947,093 A | 3/1976 | Goshima et al. |
| 3,960,449 A | 6/1976 | Carleton et al. |
| 3,963,606 A | 6/1976 | Hogg |
| 3,973,003 A * | 8/1976 | Colas ......................... 424/561 |
| 3,973,196 A | 8/1976 | Hogg |
| 4,007,087 A | 2/1977 | Ericsson |
| 4,009,260 A | 2/1977 | Ericsson ..................... 424/105 |
| 4,014,611 A | 3/1977 | Simpson et al. |
| 4,067,965 A | 1/1978 | Bhattacharya .............. 424/105 |
| 4,070,617 A | 1/1978 | Kachel et al. |
| 4,083,957 A | 4/1978 | Lang ............................ 424/78 |
| 4,085,205 A | 4/1978 | Hancock ..................... 424/105 |
| 4,092,229 A | 5/1978 | Bhattacharya .......... 204/180 R |
| 4,155,831 A | 5/1979 | Bhattacharya .......... 207/299 R |
| 4,162,282 A | 7/1979 | Fulwyler et al. |
| 4,178,936 A | 12/1979 | Newcomb |
| 4,179,218 A | 12/1979 | Erdmann et al. |
| 4,191,749 A | 3/1980 | Bryant ...................... 424/105 |
| 4,200,802 A | 4/1980 | Salzman et al. |
| 4,225,405 A | 9/1980 | Lawson .................. 204/180 R |
| 4,230,558 A | 10/1980 | Fulwyler |
| 4,255,021 A | 3/1981 | Brunsden |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson .................. 204/180 R |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson ..................... 424/105 |

(Continued)

FOREIGN PATENT DOCUMENTS

BR    9704313    6/1999

(Continued)

OTHER PUBLICATIONS

Hollinshead F.K. et al. "In vitro and in vivo assessment of functional capacity of flow cytometrically sorted ram spermatozoa after freezing and thawing." Reprod. Fertil. and Develop. 2003, vol. 15, pp. 351-359.

(Continued)

*Primary Examiner*—Sandra E. Saucier
*Assistant Examiner*—Lora E Barnhart
(74) *Attorney, Agent, or Firm*—Santangelo Law Offices, P.C.

(57) ABSTRACT

Methods and apparatus are disclosed for processing sperm cells to accomplish preservation for future use while minimizing the adverse effects of such preservation. Sperm cells may be collected from a male animal and subjected to a first preservation step, including potentially a first cryopreservation step. Preserved sperm may then be revived, including potentially by thawing, and treated by any of various processing steps to mitigate the adverse effects of preservation. Treated sperm may then be subjected to a second preservation step, including potentially a second cryopreservation step, perhaps enabling a delayed use of the sperm at a future time.

14 Claims, 2 Drawing Sheets

U.S. PATENT DOCUMENTS

| | | |
|---|---|---|
| 4,341,471 A | 7/1982 | Hogg et al. |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair ........................ 209/3.3 |
| 4,395,397 A | 7/1983 | Shapiro |
| 4,395,676 A | 7/1983 | Hollinger et al. |
| 4,400,764 A | 8/1983 | Kenyon |
| 4,422,761 A | 12/1983 | Frommer |
| 4,448,767 A | 5/1984 | Bryant ........................ 424/85 |
| 4,474,875 A | 10/1984 | Shrimpton ..................... 435/2 |
| 4,487,320 A | 12/1984 | Auer |
| 4,498,766 A | 2/1985 | Unterleitner |
| 4,501,366 A | 2/1985 | Thompson .................. 209/556 |
| 4,511,661 A | 4/1985 | Goldberg .................... 436/503 |
| 4,515,274 A | 5/1985 | Hollinger et al. |
| 4,523,809 A | 6/1985 | Toboada et al. |
| 4,538,733 A | 9/1985 | Hoffman |
| 4,559,309 A | 12/1985 | Evenson |
| 4,598,408 A | 7/1986 | O'Keefe |
| 4,600,302 A | 7/1986 | Sage, Jr. |
| 4,605,558 A | 8/1986 | Shrimpton .................. 424/561 |
| 4,631,483 A | 12/1986 | Proni et al. |
| 4,637,691 A | 1/1987 | Uehara et al. |
| 4,654,025 A | 3/1987 | Cassou et al. |
| 4,660,971 A | 4/1987 | Sage et al. ..................... 356/39 |
| 4,673,288 A | 6/1987 | Thomas et al. ............... 356/72 |
| 4,680,258 A | 7/1987 | Hammerling et al. .......... 435/7 |
| 4,683,195 A | 7/1987 | Mullis et al. ................... 435/6 |
| 4,683,202 A | 7/1987 | Mullis ......................... 435/91 |
| 4,691,829 A | 9/1987 | Auer |
| 4,698,142 A | 10/1987 | Muroi et al. ............. 204/182.3 |
| 4,702,598 A | 10/1987 | Böhmer |
| 4,714,680 A | 12/1987 | Civin |
| 4,744,090 A | 5/1988 | Freiberg |
| 4,749,458 A | 6/1988 | Muroi et al. ............. 204/182.3 |
| 4,756,427 A | 7/1988 | Gohde et al. |
| 4,758,729 A | 7/1988 | Monnin |
| 4,764,013 A | 8/1988 | Johnston |
| 4,780,451 A | 10/1988 | Donaldson |
| 4,790,653 A | 12/1988 | North, Jr. ..................... 356/73 |
| 4,794,086 A | 12/1988 | Kasper et al. |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,877,965 A | 10/1989 | Dandliker et al. |
| 4,942,305 A | 7/1990 | Sommer |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel ......................... 435/30 |
| 4,999,283 A | 3/1991 | Zavos et al. ................... 435/2 |
| 5,005,981 A | 4/1991 | Schulte et al. |
| 5,007,732 A | 4/1991 | Ohki et al. |
| 5,021,244 A | 6/1991 | Spaulding .................. 424/561 |
| 5,030,002 A | 7/1991 | North, Jr. |
| 5,034,613 A | 7/1991 | Denk et al. |
| 5,055,393 A | 10/1991 | Kwoh et al. ................... 435/6 |
| 5,079,959 A | 1/1992 | Miyake et al. |
| 5,084,004 A | 1/1992 | Ranoux |
| 5,088,816 A | 2/1992 | Tomioka et al. |
| 5,098,657 A | 3/1992 | Blackford et al. |
| 5,101,978 A | 4/1992 | Marcus |
| 5,127,729 A | 7/1992 | Oetliker et al. |
| 5,132,548 A | 7/1992 | Borden et al. |
| 5,135,759 A | 8/1992 | Johnson ..................... 424/561 |
| 5,144,224 A | 9/1992 | Larsen |
| 5,150,313 A | 9/1992 | Van den Engh et al. .... 364/569 |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,298,967 A | 3/1994 | Wells |
| 5,315,122 A | 5/1994 | Pinsky et al. |
| 5,346,990 A | 9/1994 | Spaulding .................. 530/350 |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. ............. 356/246 |
| 5,412,466 A | 5/1995 | Ogino |
| 5,437,987 A | 8/1995 | Ten et al. ................... 435/7.25 |
| 5,439,362 A | 8/1995 | Spaulding ................ 424/185.1 |
| 5,447,842 A | 9/1995 | Simons |
| 5,452,054 A | 9/1995 | Dewa et al. |
| 5,461,145 A | 10/1995 | Kudo et al. ............... 536/24.31 |
| 5,466,572 A | 11/1995 | Sasaki et al. ................... 435/2 |
| 5,467,189 A | 11/1995 | Kreikebaum et al. |
| 5,471,294 A | 11/1995 | Ogino |
| 5,471,299 A | 11/1995 | Kaye et al. |
| 5,480,774 A | 1/1996 | Hew et al. ..................... 435/6 |
| 5,483,469 A | 1/1996 | Van den Engh et al. .... 364/555 |
| 5,494,795 A | 2/1996 | Guerry et al. .................. 435/6 |
| 5,496,272 A | 3/1996 | Chung et al. |
| 5,503,994 A | 4/1996 | Shear et al. ................... 436/90 |
| 5,514,537 A | 5/1996 | Chandler ....................... 435/2 |
| 5,523,573 A | 6/1996 | Hanninen et al. |
| 5,532,155 A | 7/1996 | Ranoux |
| 5,558,998 A | 9/1996 | Hammond et al. |
| 5,578,449 A | 11/1996 | Frasch et al. ................... 435/6 |
| 5,589,457 A | 12/1996 | Wiltbank ..................... 514/12 |
| 5,596,401 A | 1/1997 | Kusuzawa |
| 5,601,235 A | 2/1997 | Booker et al. |
| 5,601,533 A | 2/1997 | Hancke et al. |
| 5,602,039 A | 2/1997 | Van den Engh ............ 436/164 |
| 5,602,349 A | 2/1997 | Van den Engh ......... 73/864.85 |
| 5,622,820 A | 4/1997 | Rossi ............................. 435/5 |
| 5,641,457 A | 6/1997 | Vardanega et al. .......... 250/207 |
| 5,643,796 A | 7/1997 | Van den Engh et al. ...... 436/50 |
| 5,650,847 A | 7/1997 | Maltsev et al. |
| 5,660,997 A | 8/1997 | Spaulding .................. 435/7.21 |
| 5,663,048 A | 9/1997 | Winkfein et al. |
| 5,672,880 A | 9/1997 | Kain |
| 5,675,401 A | 10/1997 | Wangler et al. |
| 5,684,575 A | 11/1997 | Steen |
| 5,687,727 A | 11/1997 | Kraus et al. |
| 5,690,895 A | 11/1997 | Matsumoto et al. .......... 422/73 |
| 5,691,133 A | 11/1997 | Critser et al. |
| 5,693,534 A | 12/1997 | Alak et al. |
| 5,700,692 A | 12/1997 | Sweet ........................... 436/50 |
| 5,707,808 A | 1/1998 | Roslaniec et al. |
| 5,708,868 A | 1/1998 | Ishikawa |
| 5,726,364 A | 3/1998 | Van den Engh ......... 73/864.85 |
| 5,759,767 A | 6/1998 | Lakowicz et al. |
| 5,777,732 A | 7/1998 | Hanninen et al. |
| 5,780,230 A | 7/1998 | Li et al. ......................... 435/6 |
| 5,786,560 A | 7/1998 | Tatah et al. |
| 5,793,485 A | 8/1998 | Gourley |
| 5,796,112 A | 8/1998 | Ichie |

| | | |
|---|---|---|
| 5,804,436 A | 9/1998 | Okun et al. |
| 5,815,262 A | 9/1998 | Schrof et al. |
| 5,819,948 A | 10/1998 | Van den Engh ............ 209/158 |
| 5,824,269 A | 10/1998 | Kosaka et al. |
| 5,835,262 A | 11/1998 | Iketaki et al. |
| 5,868,767 A | 2/1999 | Farley et al. |
| 5,873,254 A | 2/1999 | Arav |
| 5,876,942 A | 3/1999 | Cheng et al. .................. 435/6 |
| 5,880,457 A | 3/1999 | Tomiyama et al. ......... 250/207 |
| 5,888,730 A | 3/1999 | Gray et al. |
| 5,891,734 A | 4/1999 | Gill et al. |
| 5,895,764 A | 4/1999 | Sklar et al. |
| 5,895,922 A | 4/1999 | Ho |
| 5,899,848 A | 5/1999 | Haubrich |
| 5,912,257 A | 6/1999 | Prasad et al. |
| 5,916,144 A | 6/1999 | Prather et al. |
| 5,916,449 A | 6/1999 | Ellwart et al. |
| 5,919,621 A | 7/1999 | Brown .......................... 435/6 |
| 5,985,216 A | 11/1999 | Rens et al. .................... 422/73 |
| 5,985,538 A | 11/1999 | Stachecju |
| 6,002,471 A | 12/1999 | Quake |
| 6,050,935 A | 4/2000 | Ranoux et al. |
| 6,071,689 A | 6/2000 | Seidel et al. .................... 435/2 |
| 6,087,352 A | 7/2000 | Trout |
| 6,117,068 A | 9/2000 | Gourley et al. |
| 6,119,465 A | 9/2000 | Mullens et al. |
| 6,133,044 A | 10/2000 | Van den Engh |
| 6,140,121 A | 10/2000 | Ellington et al. |
| 6,149,867 A | 11/2000 | Seidel et al. .................. 422/73 |
| 6,153,373 A | 11/2000 | Benjamin et al. |
| 6,154,276 A | 11/2000 | Mariella, Jr. ................ 356/337 |
| 6,175,409 B1 | 1/2001 | Nielsen et al. |
| 6,177,277 B1 | 1/2001 | Soini |
| 6,238,920 B1 | 5/2001 | Nagai et al. |
| 6,248,590 B1 | 6/2001 | Malachowski |
| 6,263,745 B1 | 7/2001 | Buchanan et al. |
| 6,283,920 B1 | 9/2001 | Eberle et al. |
| 6,357,307 B2 | 3/2002 | Buchanan et al. |
| 6,372,422 B1 * | 4/2002 | Seidel et al. .................... 435/2 |
| 6,395,305 B1 | 5/2002 | Buhr et al. |
| 6,411,835 B1 | 6/2002 | Modell et al. |
| 6,463,314 B1 | 10/2002 | Haruna |
| 6,489,092 B1 | 12/2002 | Benjamin et al. |
| 6,524,860 B1 | 2/2003 | Seidel et al. |
| 6,528,802 B1 | 3/2003 | Karsten et al. |
| 6,534,308 B1 | 3/2003 | Palsson et al. |
| 6,537,829 B1 | 3/2003 | Zarling et al. |
| 6,577,387 B2 | 6/2003 | Ross, III et al. |
| 6,590,911 B1 | 7/2003 | Spinelli et al. |
| 6,604,435 B2 | 8/2003 | Buchanan et al. |
| 6,617,107 B1 | 9/2003 | Dean |
| 6,618,679 B2 | 9/2003 | Loehrlein et al. |
| 6,642,018 B1 | 11/2003 | Koller et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,704,313 B1 | 3/2004 | Duret et al. |
| 6,782,768 B2 | 8/2004 | Buchanan et al. |
| 6,819,411 B1 | 11/2004 | Sharpe et al. |
| 2002/0096123 A1 | 7/2002 | Whittier et al. |
| 2002/0113965 A1 | 8/2002 | Roche et al. |
| 2002/0119558 A1 | 8/2002 | Seidel et al. |
| 2002/0141902 A1 | 10/2002 | Ozasa et al. |
| 2002/0186375 A1 | 12/2002 | Asbury et al. |
| 2003/0098421 A1 | 5/2003 | Ho |
| 2003/0129091 A1 | 7/2003 | Seidel et al. |
| 2003/0157475 A1 | 8/2003 | Schenk |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0062685 A1 | 4/2004 | Norton et al. |
| 2004/0132001 A1 | 7/2004 | Seidel et al. |
| 2005/0003472 A1 | 1/2005 | Muhammad |
| 2005/0112541 A1 | 5/2005 | Durack |
| 2005/0214733 A1 | 9/2005 | Graham |

FOREIGN PATENT DOCUMENTS

| | | |
|---|---|---|
| EP | 0025296 A2 | 3/1981 |
| EP | 0071538 A1 | 2/1983 |
| EP | 0160201 A2 | 2/1983 |
| EP | 0189702 A1 | 8/1986 |
| EP | 0288029 B1 | 4/1988 |
| EP | 0276166 A2 | 7/1988 |
| EP | A-0 366794 | 5/1990 |
| EP | 0461618 | 12/1991 |
| EP | 0468100 A1 | 1/1992 |
| EP | 0570102 A1 | 3/1993 |
| EP | 0538786 A | 4/1993 |
| EP | A-0 478155 | 1/1998 |
| EP | 1250897 A1 | 10/2002 |
| EP | 1403633 A3 | 4/2004 |
| FR | 2574656 A1 | 6/1986 |
| FR | A-2 635453 | 2/1990 |
| FR | 2 647 668 A | 12/1990 |
| FR | 2699678 A1 | 6/1994 |
| JP | 61139747 A | 6/1986 |
| JP | 61159135 A | 7/1986 |
| JP | 2024535 | 1/1990 |
| JP | 4126064 A | 4/1992 |
| JP | 4126065 A | 4/1992 |
| JP | 4126066 A | 4/1992 |
| JP | 4126079 A | 4/1992 |
| JP | 4126080 A | 4/1992 |
| JP | 4126081 A | 4/1992 |
| JP | EP 606847 A2 | 7/1994 |
| NZ | WO 98/34094 | 8/1998 |
| SU | 1056008 | 11/1983 |
| SU | 1260778 A1 | 9/1986 |
| WO | WO 88/07198 | 9/1988 |
| WO | WO 90/13315 A1 | 11/1990 |
| WO | WO 96/12171 | 4/1996 |
| WO | WO 96/31764 | 10/1996 |
| WO | WO 98/48259 | 10/1998 |
| WO | WO 99/05504 | 2/1999 |
| WO | WO 99/33956 | 7/1999 |
| WO | WO 99/38883 | 8/1999 |
| WO | WO 99/42810 | 8/1999 |
| WO | WO 99/44037 A1 | 9/1999 |
| WO | WO 00/06193 | 2/2000 |
| WO | WO 01/37655 A1 | 5/2001 |
| WO | WO 01/40765 A2 | 6/2001 |
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02/28311 A2 | 4/2002 |
| WO | WO 02/41906 A2 | 5/2002 |
| WO | WO 02/43486 A1 | 6/2002 |
| WO | WO 02/43574 A2 | 6/2002 |
| WO | WO 04/009237 A2 | 1/2004 |
| WO | WO 04/009237 A3 | 1/2004 |
| WO | WO 04/012837 A2 | 2/2004 |
| WO | WO 04/012837 A3 | 2/2004 |
| WO | WO 04/017041 A2 | 2/2004 |
| WO | WO 04/017041 A3 | 2/2004 |
| WO | WO 04/024227 A2 | 3/2004 |
| WO | WO 2004/059282 A2 | 7/2004 |
| WO | WO 2004/003697 A2 | 10/2004 |

| | | | |
|---|---|---|---|
| WO | WO 2004/087177 A1 | 10/2004 |
| WO | WO 2004/088283 A2 | 10/2004 |
| WO | WO 04/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |

OTHER PUBLICATIONS

Hollinshead F.K. et al. "Production of lambs of predetermined sex after the insemination of ewes with low numbers of frozen-thawed sorted X- or Y-Chromosome-bearing spermatozoa", Reprod. Fertil. and Develop. 2002, vol. 14, pp. 503-508.

Hollinshead F.K, et al. "Sex-Sorting and Re-cryopreservation of Frozen-Thawed Ram Sperm for In Vitro Embryo Production", Theriogenology vol. 59, (2003), pp. 209.

Schenk, J. L. et al. "Cryopreservation of flow-sorted bovine spermatozoa", Theriogenology vol. 52, (1999), pp. 1375-1391.

Seidel, G., "Economics of selecting for sex: The Most Important Genetic Trait", Theriogenology 59, (2003), pp. 585-598.

Stap J. et al. "Improving the resolution of cryopreserved X- and Y-sperm during DNA flow cytometric analysis with the addition of percoll to quench the fluorescence of dead sperm", Journal of Animal Science, 1998, vol. 76, pp. 1896-1902.

Amann, R.P. et al, "Prospects For Sexing Mammalian Sperm," Colorado Associated University Press, Animal Reproduction Laboratory College of Veterinary Medicine and Biomedical Sciences, Colorado State University, Fort Collins, CO, 80523, 1982, Table of Contents Only.

Becker, S.E. and Johnson, A.L. "Effects of gonadotropin releasing hormone infused in a pulsatite or continuous fashion on serum gonadotropin concentrations and ovulation in the mare", J. Anim. Sci. 70:1208-1215. (1992).

Bedford, S .J. and Hinrichs, K., "The effect of insemination volume on pregnancy rates of pony mares", Theriogenology 42:571-578. (1994).

Berger, G.S. "Intratubal insemination", Fert. Steril. 48:328-330, (1987).

Blanchard, T. and Dickson, V., "Stallion Management", The Veterinary Clinics of North America, Equine Practice, vol. 8, No. 1, pp. 207-218 (1992) pp. 212-216 Missing.

Bracher, V. and Allen, W.R., "Videoendoscopic Examination of the Mare's Uterus: Findings in Normal Fertile Mares", Equine Veterinary Journal, vol. 24 (1992), pp. 274-278.

Burwash, L.D., Pickett, B.W., Voss, J.L. and Back, D.G. 1974. "Relationship of duration of estms to pregnancy rate in normally cycling, non-lactating mares" J.A.V.M.A. 165:714-716.

Catt, et al., "Assessment of Ram and Boar Spermatozoa During Cell-Sorting by Flow Cytometry", Reproduction Dom Animal, vol. 32, pp. 251-258 (1997).

Clement, F., Vincent, P., Mahla, R., Meriaux, J.C. and Palmer, E. 1998. Which insemination fertilizes when several successive inseminations are performed before ovulation. J. Reprod Fert. Suppl. 56:579-585.

Cran, D.G., et al., "Production of Lambs by Low Dose Intrauterine Insemination with Flow-Cytometrically Sorted and Unsorted Semen", Theriogenology 47, 1997, p. 267.

Curran, S. 1998. In: Equine Diagnostic Ultrasonography. Fetal gender determination. Rantanen & McKinnon. 1st Ed. Williams and Wilkins. pp. 165-169.

Dean, P.N., Pinkel, D. and Mendelsob. n, M.L. 1978. Hydrodynamic orientation of spermatozoa heads for flow cytometry. Biophys. J. 23:7-13.

Demick, D.S., Voss, J.L. and Pickett, B.W. 1976. Effect of cooling, storage, glycerization and spermatozoal numbers on equine fertility. J. Anim. Sci. 43:633-637.

DenDaas, J.H.G., De Jong, G., Lansbergen, L.M.T.E. and Van Wagtendonk-De Leeuw, A.M. 1998. The relationship between the number of spermatozoa inseminated and the reproductive efficiency of dairy bulls. J Dairy Sci. 81: 1714-1723.

Donaldson, L. E., "Effect of Insemination Regimen on Embryo Production in Superovulated cows", The Veterinary Record, Jul. 13, 1985, pp. 35-37.

Donoghue, A.M., Byers, A.P., Johnston, L.A., Armstrong, D.L. and Wildt, D.E. 1996. Timing of ovulation after gonadotropin induction and its importance to successful intrauterine insemination in the tiger (*Panthera tigris*). J. Reprod. Fert. 107:53-58.

Douglas, R.H. 1979. Review of superovulation and embryo transfer in the equine. Theriogenology. 11:33-46.

Douglas, R.H., Nuti, L. and Ginther, O.J. 1974. Induction of ovulation and multiple ovulation on seasonally-anovulatory mares with equine pituitary fractions. Theriogenology. 2(6): 133-142.

Duchamp, G., Bour, B., Combamous, Y. and Palmer, E. 1987. Alternative solutions to hCG induction of ovulation in the mare. J. Reprod. Fert. Suppl. 35:221-228.

Evans, M.J. and Irvine, C.H.G. 1977. Induction of follicular development, maturation and ovulation by gonadotropin releasing hormone administration to acyclic mares. Bio. Reprod. 16:452-462.

Fitzgerald, B.P., Peterson, K.D. and Silvia, P.J. 1993. Effects of constant administration of a gonadotropin-releasing hormone agonist on reproductive activity in mares: Preliminary evidence on suppression of ovulation during the breeding season. Am. J. Vet. Res. 54:1746-1751.

Fluharty, F. L., et al., "Effect of weaning and diet on growth of calves." Research and Reviews. The Ohio State University Department of Animal Sciences. 1996.

Garner, D.L., et al., 1983. Quantification of the X and Y chromosome-bearing spermatozoa of domestic animals by flow cytometry. Biol. Reprod. 28:312-321.

Ginther, O.J. 1983. Sexual behavior following introduction of a stallion into a group of mares. Theriogenology, 19:877.

Guillou, F. and Combamous, Y. 1983. Purification of equine gonadotropins and comparative study of their acid-dissociation and receptor-binding specificity. Biochem. Biophys. Acta. 755:229-236.

Hawk, H.W., et al., "Fertilization Rates in Superovulating Cows After Deposition of Semen on the Infundibulum Near the Uterotubal Junction or After Insemination with High Numbers of Sperm", XP-002103478, Theriogenology, May 1988, vol. 29, No. 5, pp. 1131-1142.

Hofferer, S., Lecompte, F., Magallon, T., Palmer, E. and Combamous, Y. 1993. Induction of ovulation and superovulation in mares using equine LH and FSH separated by hydrophobic interaction chromatography. J. Reprod. Fert. 98:597-602.

Irvine, C.H.G. and Alexander, S.L. 1993. *In:* Equine Reproduction. Edited by McKinnon and Voss. Lea and Febiger. Philadelphia, London. pp. 37.

Jafar, et al., "Sex Selection in Mammals: A Review", Theriogenology, vol. 46, pp. 191-200 (1996).

Johnson, L., "Sex Preselection by Flow Cytometric Separation of X and Y Chromosome-Bearing Sperm Based on DNA Difference: a Review", Reproduction and Fertilization Development 7, 1995, pp. 893-903.

Johnson, L., "Sex Preselection in Swine: Flow Cytometric Sorting of X- and Y- Chromosome Bearing Sperm to Produce Offspring", Boar Semen Preservation IV, 2000, pp. 107-114.

Johnson, L., "Successful Gender Preselection in Farm Animals", Agricultural Biotechnology, 1998, pp. 439-452.

Johnson, L.. A., "Sex Preselection in Rabbits: Live Births from X and Y Sperm Separated by DNA and Cell Sorting" Biology of Reproduction, vol. 41, pp. 199-203 (1989).

Johnson, L.A., and Pinkel, D., "Modification of a Laser-Based flow Cytometer for High-Resolution DNA Analysis of Mammalian Spermatozoa", Cytometry 7, 1986, pp. 268-273.

Johnson, L.A., et al., "Enhanced flow cytometric sorting of mammalian X and Y sperm: high speed sorting and orienting nozzle for artificial insemination", Theriogenology. 49(1):361 abstr., 1988.

Johnson, L.A., et al., "Flow sorting of X and Y chromosome bearing spermatozoa into two populations", Gam. Res. 16:203-212, 1987.

Karabinus, et al., "Effects of Egg Yolk-Citrate and Milk Extenders on Chromatin Structured Viability of Cryopreserved Bull Sperm", Journal of Dairy Science, vol. 74, No. 11, 1991, pp. 3836-3848.

Levinson, G., et al., 1995. DNA-based X-enriched sperm separation as an adjunct to preimplantation genetic testing for the preparation of X-linked disease. Mol. Human Reprod. 10:979-982.

Martinez, E.A., et al., "Successful Low-Dose Insemination by a Fiberoptic Endoscope Technique in the Sow", Proceedings Annual Conference of the International Embryo Transfer Society, Netherlands, Theriogenology, vol. 53, Jan. 2000, pp. 201.

McCue, P.M. 1996. Superovulation. Vet. Clin. N. Amer. Eq. Prac. 12:1-11.

McCue, P.M., et al., 1997. Oviductal insemination in the mare. 7th Int Symp. Eq. Reprod. 133. abstr.

McKenna, T. et al., 1990. Nonreturn rates of dairy cattle following uterine body or cornual insemination. J. Dairy Sci. 73:1179-1783.

McKinnon, A. and Voss, J., "Equine Reproduction", Lea & Febiger, Philadelphia, 1993, pp. 291, 299-302, 345-348, 739-797.

McKinnon, A.O. et al, 1996. Repeated use of a GnRH analogue deslorelin (Ovuplant) for hastening ovulation in the transitional mare. Eq. Vet. J. 29:153-155.

McNutt, et al., "Flow Cytometric Sorting of Sperm: Influence on Fertilization and Embryo/Fetal Development in the Rabbits", Molecular Reproduction and Development, vol. 43, pp. 261-267 (1996).

Meinert, C., et al., "Advancing the time of ovulation in the mare with a short-term implant releasing the GnRH analogue deslorelin", Equine Veterinary Journal, 25, 1993, pp. 65-68.

Meyers, P.J., Bowman, T., Blodgett, G., Conboy, H.S., Gimenez, T., Reid, M.P., Taylor, B.C., Thayer, J.

Jochle, W. and Trigg, T.E. 1997. Use of the GnRH analogue, deslorelin acetate, in a slow release implant to accelerate ovulation in oestrous mares. Vet. Rec. 140:249-252.

Michaels, Charles, "Beef A.I. Facilities that work", Proc. Fifth N.A.A.B Tech. Conf. A.I. Reprod. Columbia, MO. pp. 20-22, date?.

Morcom, C.B. and Dukelow, W.R. 1980. A research technique for the oviductal insemination of pigs using laparoscopy. Lab. Anim. Sci. 1030-I031.

Morris, L.H., et al., "Hysteroscopic insemination of small numbers of spermatozoa at the uterotubal junction of preovulatory mares", Journal of Reproduction and Fertility, vol. 118, pp. 95-100 (2000).

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pickett, B.W., and Shiner, K.A., "Recent developments in artificial insemination in horses", Livestock Production Science, 40, pp. 31-36 (1994).

Pinkel, D., et al., "Flow Cytometric Determination of the Proportions of X- and Y- Chromosome-Bearing Sperm in Samples of Purportedly Separated Bull Sperm", Journal of Animal Science, vol. 60, No. 5, 1985, pp. 1303-1307.

Rath, D., et al., "Low Dose Insemination Technique in the Pig", Boar Semen Preservation IV, 2000, pp. 115-118.

Rath, D., et al., "Production of Piglets Preselected for Sex Following in Vitro Fertilization with X and Y Chromosome-Bearing Spermatozoa Sorted by Flow Cytometry", Theriogenology, 47, 1997, pp. 795-800.

Rens, W., et al., "Improved Flow Cytometric Sorting of X- and Y- Chromosome Bearing Sperm: Substantial Increase in Yield of Sexed Semen", Molecular Reproduction and Development, 1999, pp. 50-56.

Schmid R.L., et al, "Fertilization with Sexed Equine Spermatozoa Using Intracytoplasmic Sperm Injection and Oviductal Insemination ", 7th International Symposium On Equine Reproduction, pp. 139 (Abstract) (1998).

Seidel G.E. Jr., et al., "Insemination of Holstein Heifers With Very Low Numbers Of Unfrozen Spermatozoa.", Colorado State University, Fort Collins, Atlantic Breeders Cooperative, Lancaster, PA., DUO Dairy, Loveland, CO. Jul. 1995, ABS only.

Seidel G.E. Jr., et al., "Uterine Horn Insemination of Heifers With Very Low Numbers of Nonfrozen and Sexed Spermatozoa,", Animal Reproduction and Biotechnology Laboratory Colorado State University, Atlantic Breeders Cooperative, Lancaster, PA 17601, Germplasm and Gamete Physiology Laboratory ARS, USDA, Beltsville, MD 20705, DUO Dairy, Loveland, CO 80538, Theriogenology 48: 1255-1264, 1997.

Seidel, G.E. et al, "Artificial Insemination With X-and Y-Bearing Bovine Sperm", Animal Reproduction and Biotechnology Laboratory, Colorado State University, Fort Collins, CO; Germplasm and Gamete Physiology Lab, ARS, USDA, Beltsville, MD; Atlantic Breeders Coop, Lancaster, PA; DUO Diary, Loveland, CO, USA Jan. 1996.

Seidel, G.E. Jr., Cran, D.G., Herickoff, L.A., Schenk, J.L., Doyle, S.P. and Green, R D 1999. Insemination of heifers with sexed frozen or sexed liquid semen. Theriogenology. 51. (in press). abstr.(1999).

Seidel, G.E., et al, "Insemination Of Heifers With Very Low Numbers Of Frozen Spermatozoa", Colorado State University, Fort Collins, Atlantic Breeders Cooperative, Lancaster, PA, DUO Dairy, Loveland, CO, Jul. 1996, ABS only.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, pp. 127-130 (1996).

Squires, E.L, Moran, D.M., Farlin, ME., Jasko, D.J., Keefe, T.J., Meyers, S.A., Figueiredo, E., McCue, P.M. and Jochle, W. 1994. Effect of dose of GnRH analogue on ovulation in mares. Theriogenology. 41:757-769.

Sullivan, J.J., Parker, W.G. and Larson, LL. 1973. Duration of estrus and ovulation time in nonlactating mares given human chorionic gonadotropin during three successive estrous periods. J.A.V.M.A. 162:895-898.

Taljaard, T.L., Terblanche, S.J., Bertschinger, H.J. and Van Vuuren, L.J. 1991. The effect of the laparoscopic insemination technique on the oestrus cycle of the ewe. J. S Afr. Vet. Assoc. 62(2):60-61.

Van Munster, E.B., et al, "Difference in Sperm Head Volume as a Theoretical Basis for Sorting X & Y- Bearing Spermatozoa: Potentials and Limitations", Therio 52, pp. 1281-1293 (1999).

Vazquez, J. et al., "Nonsurgical Uterotubal Insemination in the Mare", Proceedings of the 44th Annual Convention of the American Association of Equine Practitioners, vol. 44, pp. 68-69 (1998).

Vidament, M., Dupere, A.M., Julienne, P., Evain, A., Noue, P. and Palmer, E. 1997. Equine frozen semen freezeability and fertility field results. Theriogenology. 48:907.

Voss, J.L., et al., 1982. Effect of number and frequency of inseminations on fertility in mares. J. Reprod. Fertil. Suppl. 32:53-57.

Welch, G., et al., "Flow Cytometric Sperm Sorting and PCR to Confirm Separation of X- and Y- Chromosome Bearing Bovine Sperm", Animal Biotechnology, 6 (2), 131-139, 1995.

Abdel-Ghaffar, A. E. et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Amoah, E. A. and Gelaye, S., "Biotechnological Advances in Goat Reproduction", J. Anim. Sci. 75(2): 578-585. (1996).

Anderson, V. K., et al., Intrauterine und tiefzervikale Insemination mit Gefriersperma bein Schat (Intrauterine and Deep Cervical Insemination With Frozen Semen in Sheep). Zuchthygiene 8:113-118. (1973).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Baker, R.D., et al., "Effect of Volume of Semen, Number of Sperm and Drugs on Transport of Sperm in Artificially Inseminated Gifts", J. Anim. Sci. 27:88-93. (1968).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., "Sexual Dimorphism in IVF Bovine Embryos Produced by Sperm Sorted by High Speed Flow Cytometry", abstr. Therio. 49(1): 359 (1998).

Beyhan, Z., Et Al, 1999 Sexual Dimorphism In IVM-IVF Bovine Embryos Produced from X and Y Chromosome-Bearing Spermatozoa Sorted By High Speed Flow Cytometry. Theriogenology. 52: 35-48.

Bigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef -Production III. Culling Strategies and Nontraditional Management-Systems", J. Anim. Sci. 65:963. 1987.

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al. "Effect on Different Protein Supplements on Motility and Plasma Membrane Integrity of Frozen- Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.

Burns, P. D. and Spitzer, J.C., "Influence of Biostimulation on Reproduction in Postpartum Beef-Cows", J. Anim. Sci. 70:358. 1992.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1987, p. 28.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers Witn 600,000 Sexed Sperm". J Anim. Sci. Suppl. 1. 836:215. 1998 abstr.

Cran, D. G., et al., "Sexed Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

da Silva, Coutinho M.A.. "Effect of time of oocyte collection and site of insemination on oocyte transfer in mares." Animal Reproduction and Biotechnology Laboratory, Colorado State Uniuversity, Fort Collins Journal of Animal Science 2002. 80:1275-1279.

*DakoCytomation, "MoFlo® Sorters"* http://www.dakocytomation. us/prod_productrelatedinformation?url=gprod_moflo_index. htm_one page, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www. Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNA content of Living Spermatozoa Using Flow Cytometry Technique Journal of Reproduction and Fertility, 1993, vol. 98, pp. 357-365.

Ferrell, C. L. Effects of Post-Weaning Rate of Gain on Onset of Puberty and Productive Performance of Heifers on Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234, 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Foote, et al. Motility and Fertility of Bull Sperm Frozen- Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Nouveau et tres simple dispositif interferentiel applicable as microscope" Optica Acta 9, p. 395-408.1962.

Fugger, E. F. "Clinical Experience with Flow Cytometric Separation of Human X- and Y- Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing☐Hormone (LH) and Progesterone Levels in Heifers on Restricted Energy Intakes." J. Anim. Sci. 37:728. 1973.

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. ABSTRACT Complete article from Reproductive Technology vol. 12 # Apr. 1, 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production.* 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal☐Weaned Calves". I. Prod. Agric. 4:168 (1991).

Grondahl, C., et al, "In Vitro Production of Equine Embryos", Biology of Reproduction, Monograph Series I, p. 299-307 (1995).

Gurnsey, M. P., and Johnson, L.A., "Recent Improvements in Efficiency of Flow Cytometric Sorting of X and Y-Chromosomes Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu, *"Technical Information, Optical Detector Selection: A Delicate Balancing Act"*, web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beef Production.* 123 (1975).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Hilton, G. G., et al., "An Evaluation of Current and Alternative Systems for Quality Grading Carcasses of Mature Slaughter Cows." J. Anim. Sci. 76:2094. 1998.

Ho, L., et al. "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious furo*) and Pregnancies After Laparoscopic Intrauterine Insemination With Frozen-Thawed Spermatozoa," J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

IMV Technologies, Protocol of Bioxcell with Fresh Semen, 1 page, 2000.

IMV Technologies, Protocol of Bioxcell with Frozen Semen, 2 pages, 2000.

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol 17, No. 3, pp. 732-735.

Jarriage, R. "Age of Cows at First Calving in France." In: J.C. Taylor (Ed.) *The Early Calving of Heifers and its Impact on Beef Production.* 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection in Swine: Altered Sex Rations in Offspring Following Surgical Insemination of Flow Sorted X- and Y- Bearing Sperm", Reproduction in Domestic Animals, vol. 26, pp. 309-314 (1991).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytometry of X- and Y-Chromosome Bearing Sperm for DNA Using an Improved Preparation Method and Staining with Hoechst 33342." Gamete Research 17: 203-212. (1987).

Joseph, R. L. "Carcass composition and meat quality in once calved heifers." In: J.C. Taylor (Ed.) *The Early Calving of Heifers and its Impact on Beef Production.* 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Region Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Lindsey, A. C., et al., "Low Dose Insemination of Mares Using Non-Sorted and Sex-Sorted Sperm" Animal Reproduction Science 68 p. 279-89 (2001).

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production.* (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKinnon, A.O., et al., "Predictable Ovulation in Mares Treated With an Implant of the GnRH Analogue Deslorelin." Eq. Vet. J. 25:321-323. (1993).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm preparation protocols" Theriogenology 60 (2003) 331-340.

Menke,E. A Volume Activated Cell Sorter Journal of Histo chemistry and Cyto Chemistry, 1977, vol. 25,No.7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Bree. Abstr. 5:387. (1937).

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morgan, J. b., et al., "National Beef Tenderness Survey." J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationships of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers," J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microfus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rathi, R. et al., "Evaluation of In Vitro Capacitation of Stallion Spermatozoa", Biology of Reproduction 2001, vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysteroscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roser, J. F., et al., "Reproductive Efficiency in Mares With AntihCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) (1961 & 1978 COMBINED) Chapters 16 and 17 are the complete article.

Schenk, J. L. "Applying Semen Sexing Technology to the AI Industry", Proceedings of the 18th Technical Conference on Artificial Insemination & Reproduction, 2000.

Schenk, J. L, et al., "Imminent Commercialization of Sexed Bovine Sperm", Proceedings, The Range Beef Cow Symposium XVL, p. 89-96 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. Sexing mammalian spermatozoa and embryos-state of the art Journal of Reproduction and Fertility Supp 54, 477-487 1999.

Seidel, G. E. Jr et al., "Current Status of Sexing Mammalian Spermatozoa," Society for Reproduction and fertility, pp. 733-743, 2002.

Seidel, G. E. Jr., "Commercilizing Repreductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr. "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Senger, P. L., et al., "Influence of Cornual Insemination on Conception in Dairy Cattle." J. Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometric Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 ABSTRACT.

Sharpe, Johnathan, Thesis; "An Introductory of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1-, (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Solsberry, G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Staigmiller, R.B. "Superovulation of Cattle with Equine Pituitary Extract and Porcine FSH" Theriogenology 37: 1091-1099 1992.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sumner, A. T. and Robinson, J. A., "A Difference in Dry Mass Between the Heads of X and Y- Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Tatum, J. D., et al., "Carcass Characteristics, Time on Feed and Cooked Beef Palatability Attributes." J. Anim. Sci. 50:833. (1980).

Tervit, H.R., et al., "Successful Culture In Vitro of Sheep and Cattle Ova" Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., "Geslachtsbepaling met interferometrie", Derde prijs NtvN-prijsvraag voor pas-gepromoveerden 65/4, (Sex Determination with Interferometry) p. 95-98 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al., "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. M., et al., "A. I. in Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservation of Spermatozoa and the Assessment of Their Post-Thawing Function," Reprod. Fertil. Dev. 7:871-891 (1995) Abstract.

Welch G., et al., Fluidic and Optical Modifications to a FACS IV for Flow Sorting of X- and Y- Chromosome Bearing Sperm Based on DNA. Cytometry 17 (Suppl. 7): 74. (1994).

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schulz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer Et al.:"Krankheiten des Pferdes Ein Leitfaden fur Studium und Praxiz," 1982, nParey. Berlin Hamburg XP002281450.

Woods, G. L. and Ginther, O. J. "Recent Studies Related to the Collection of Multiple Embryos in Mares," Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Hamamatsu, "Photomultiplier Tubes," web page, http://www.optics.org/hamamatsu/pmt.html. Printed on Apr. 15, 2000 4.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Dhali et al. Vitrification of Buffalo (Bubalus Bubalis)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertilization and AI, Journal of Animal Science, vol. 77, Suppl 2/J, Dairy Sci. vol. 82, Suppl. Feb. 1999 pp. 213-220.

Peters D., The LLNl high-speed sorter: Design features,operational characteristics, and bioloical utility, Cyometry, 6:290-301 (1985).

Rens W., et al Slit-scan flow cytometry for consistent high resdolution DNA analysis of X- and Y- chromosome bearing sperm, Cytometry 25:191-199 (1996).

van Munster, E. B. Interferometry in flor to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/Isrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (Bos taurus) by dual colour flourescence in situ hybridization; J Anim Breed Genet. Apr. 2005; 122 Suppl 1:22-7 (Abstract Only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilisation of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

* cited by examiner

SPERM CELL PROCESSING AND PRESERVATION SYSTEMS

BACKGROUND OF THE INVENTION

Fertilization techniques such as artificial insemination and in vitro fertilization techniques have been conducted in attempt to increase the fertility rates of livestock. Furthermore, effective pre-selection of sex has been accomplished in many species of livestock following the development of safe and reliable methods of sorting, generally, or specifically separating sperm cells into enriched X chromosome bearing and Y chromosome bearing populations. Separation of X chromosome bearing sperm cells from Y chromosome bearing sperm cells, as well as collection, handling, sorting, separation, storage, transportation, use, fertilization, or insemination techniques, or sperm cell and semen processing generally, can be accomplished as disclosed herein and as disclosed by various patent applications, for example: PCT/US99/17165; PCT/US01/45023; PCT/US01/15150; PCT/US98/27909; PCT/US01/45237, PCT/US01/18879, PCT/US00/30155, PCT/US01/02304, U.S. Pat. Nos. 6,071,689, 6,372,422, U.S. divisional application No. 10/081,955, U.S. provisional application No. 60/400,486, and U.S. provisional application No. 60/400,971, each included in Exhibit A attached, and each hereby incorporated by reference herein.

Although the various devices and methods of sperm cell processing, generally, and the collection, handling, separation, storage, transportation, usage, fertilization, and insemination of sperm cells have been improved over the past several years, significant problems remain with respect to maintaining sperm quality, such as viability, motility, functionality, and preservation and stimulation relative to such techniques, especially with regard to artificial insemination (in vivo) and in vitro fertilization (IVF) procedures. One potential consequence is the reduction in fertility rates. Sperm quality, such as the viability of sperm separated into enriched X-chromosome bearing and Y-chromosome bearing populations could be compared directly in-vitro (for example, in conjunction with IVF procedures) and in-vivo (for example, in conjunction with artificial insemination procedures), is generally reduced during traditional sperm cell processing. More generally, traditional processing techniques addressing sperm viability, motility, functionality, preservation, stimulation, fertilization, and insemination may have not yielded preferred fertility rates, insemination rates, fertilization rates, or sperm quality, generally.

As one example of traditional sperm processing, techniques of sperm sorting for the breeding of mammals may be limited, for example, with regard to sperm cell quality, such as sperm cell viability, and fertility rates, in circumstances wherein the sorter apparatus is a relatively long distance from the males or when the sorter apparatus is a relatively long distance from the receiving females to be inseminated or otherwise fertilized with processed sperm. Some of the techniques incorporated by reference may achieve to some degree sperm cell viability, motility, or functionality, and desirable fertility rates, while addressing, for example, sperm preservation during transportation to the sorter apparatus. However, further techniques achieving sufficient sperm cell quality, such as viability, motility, functionality, stimulation, and preservation, and maintained or enhanced fertility rates, insemination rates, fertilization rates, may be desirable, especially for any one or a combination of various sperm processing steps, such as, for example, collection, handling, separation, storage, transportation, usage, fertilization, or insemination of semen or sperm cells, especially the preservation of the sorted sperm cells from the sorter apparatus to the site of fertilization (potentially via collected individual samples or "straws"), or at any other stage of sperm processing.

As another example of the limitations of traditional sperm processing, traditional processing techniques may be limited with regard to sperm cell quality, generally, such as sperm cell viability, motility, functionality, stimulation, and preservation, as well as fertility rates, insemination rates, fertilization rates, due to the type and the extent processing involved. Known processing techniques such as preservation or sorting, for example, may degrade sperm quality, and further reduce fertility rates, insemination rates, and fertilization rates. The degradation of sperm quality and/or the reduction of fertility rates, insemination rates, and fertilization rates may have previously proven problematic in circumstances that may have required further steps of sperm cell preservation, such as in circumstances wherein the sorter apparatus is a relatively long distance from the males or when the sorter apparatus is a relatively long distance from the receiving females to be inseminated or otherwise fertilized with processed sperm.

It may have been traditionally understood that additional processing steps in the processing of sperm cells or semen having a concentration of sperm cells would degrade sperm quality and reduce fertility rates, insemination rates, and fertilization rates to such an extent that additional processing steps, generally, would be avoided. Specifically, it may also have been traditionally understood that processing steps such as preservation, specifically cryopreservation, and sorting might be too damaging to the sperm cells, especially in processing sequences incorporating both cryopreservation and sorting. Furthermore, it may have even been suggested and taught in traditional methods that preservation of sperm, such as cryopreservation, provided after previous processing steps so as to preserve the sperm for later procedures, such as for in vivo or in vitro techniques, could not be accomplished without compromising the sperm cells and the technique itself to such a degree that the results of the later procedures would be detrimentally affected. Accordingly, such concerns may have even been demonstrated in traditional sperm cell processing procedures, teaching away from subsequent processing steps such as sorting and cryopreservation, or processing steps incorporating multiple cryopreservation steps.

SUMMARY OF THE INVENTION

The present invention addresses the variety of previously identified and potentially unaddressed problems associated with reduced sperm cell quality, such as viability, motility, functionality, stimulation, and of preservation. Sperm cells that may have been or will be processed by one or more steps of collection, handling, separation, storage, transportation, usage, fertilization, or insemination and potential reductions in fertility rates, insemination rates, or fertilization rates are further addressed. The instant invention also addresses the variety of problems associated with sperm cell quality of sperm cells that have been separated into enriched X-chromosome bearing and Y-chromosome bearing populations, potentially sperm cells separated or sorted through techniques such as flow sorting, and the potential reduction in fertility rates. More generally, the present invention addresses traditionally low fertility rates of in vivo artificial insemination and in vitro fertilization, and sperm cell quality issues such as sperm cell viability, motility, functionality, stimulation, and preservation, as well as fertility rates, insemination rates, fertilization rates, achieving results that may have been unexpected to those skilled in the art. Additionally, the present invention addresses numbers of processed sperm potentially needed to obtain desired pregnancy rates, and further in consideration of pregnancy rates obtained respective of sorted and unsorted preserved sperm.

Accordingly, broad objects of the present invention are to provide systems to address sperm cell quality, such as viability, motility, functionality, and preservation, and to address fertilization rates, insemination rates, and fertilization rates. Each of the broad objects of the present invention may be directed to one or more of the various and previously described concerns.

One object of the present invention is to provide methods and systems of semen and sperm cell processing and preservation, and methods and systems of producing a mammal and methods of producing mammalian embryos. A further object of the present invention is to provide preservation, stimulation, fertilization, and insemination, potentially provided alone or in combination with any one or a combination of various sperm processing steps, such as, for example, collection, handling, separation, storage, transportation, usage, fertilization, or insemination of semen or sperm cells. One related object is to provide such systems in relation to the preservation of sperm cells and one or more sequences of sperm cell processing, such as the preservation of sorted sperm cells, and further in some instances, for example, preservation to a sorter apparatus, preservation from a sorter apparatus, preservation to the site of fertilization (potentially via individual sperm samples or "straws"), or at any other stage of sperm processing.

A related object of the invention is to provide systems of collection, handling, separation, storage, transportation, usage, fertilization, or insemination for semen or sperm cells to achieve desirable levels of fertility rates. One related goal is to provide systems of collection, handling, separation, storage, transportation, usage, fertilization, or insemination to maintain and enhance sperm viability, motility, functionality, preservation, stimulation, and levels of fertility rates.

A third object is to address sperm cell quality, such as sperm cell viability, motility, functionality, stimulation, and preservation, as well as fertility rates, in the context of fertilization and insemination, and in some embodiments, in the context of in vivo or in vitro techniques. A related goal of the present invention is to provide systems that achieve desirable levels of fertility rates. A second goal of the present invention is to provide systems that achieve desirable levels of fertility rates in combination with collection, handling, separation, storage, transportation, fertilization, or insemination techniques, and combinations of such techniques. A third goal of the present invention is to provide systems that achieve individual sperm samples of processed sperm cells, such as straws, of desired viability, motility, functionality, preservation, stimulation, or other characteristics, or combinations of characteristics, potentially resulting in desirable levels of fertility rates. Another related goal is to provide systems that achieve sufficient numbers of processed sperm potentially needed to obtain desired pregnancy rates, and further in consideration of pregnancy rates obtained respective of processing techniques, such as the sorting of sperm cells, and in some cases, sperm or sperm cells previously preserved.

A further object is to address sperm cell quality, such as sperm cell viability, motility, functionality, stimulation, and preservation, as well as fertility rates, insemination rates, fertilization rates, for semen or sperm cells obtained from various species of mammals, including, but not limited to equids, bovids, felids, ovids, canids, buffalo, oxen, elk, or porcine; or obtained from prize, endangered, or rare individuals of a mammal species; or obtained from zoological specimens. A related goal of the present invention, therefore, is to address sperm cell quality, generally, such as sperm cell viability, motility, functionality, stimulation, and preservation, as well as fertility rates, insemination rates, fertilization rates, for semen or sperm cells obtained from various species, individuals, and specimens so as to maintain or enhance sperm viability, motility, functionality, preservation, stimulation, fertility rates, or other characteristics, or combinations of characteristics.

Another object of the invention is to provide systems of collection, handling, separation, storage, transportation, usage, fertilization, or insemination for semen or sperm cells obtained from various species of mammals, including, but not limited to equids, bovids, felids, ovids, canids, buffalo, oxen, elk, or porcine; or obtained from prize, endangered, or rare individuals of a mammal species; or obtained from zoological specimens. A related goal of the present invention, therefore, is to provide systems of collection, handling, separation, storage, transportation, usage, fertilization, or insemination for semen or sperm cells obtained from various species, individuals, and specimens so as to maintain or enhance sperm viability, motility, functionality, preservation, stimulation, fertility rates, or other characteristics, or combinations of characteristics.

An object of the present invention is to provide systems that achieve individual samples of processed sperm, such as straws, of desired sperm cell quality, such as sperm cell viability, motility, functionality, stimulation, and preservation, or other characteristics, or combinations of characteristics, as well as providing desirable levels of fertility rates, insemination rates, or fertilization rates.

Another significant object of the invention is to provide systems of sperm cell separation that can maintain or enhance a greater sperm cell quality, such as sperm cell viability, motility, functionality, stimulation, and preservation, or other characteristics, or combination of characteristics, as well as fertility rates, insemination rates, fertilization rates, for sperm cells throughout a flow sorting process such as a process incorporating a flow cytometer.

Another significant object of the invention can be to provide systems of maintaining or enhancing sperm cells at greater sperm cell quality, such as sperm cell viability, motility, functionality, stimulation, and preservation, or other characteristics, or combination of characteristics, as well as fertility rates, insemination rates, or fertilization rates, for purposes of in vivo insemination or in vitro fertilization of various species, such as those described above, or even insemination with a low or reduced number of sperm cells compared to the usual number or typical number of sperm cells used in such insemination procedures whether or not such sperm cells are separated into enriched X chromosome bearing or Y chromosome bearing sperm cells.

Naturally, further significant objects and goals of the invention are disclosed and clarified in the proceeding description of the invention.

Accordingly, to achieve the various objects and goals of the invention, the present invention in one embodiment is a method of sperm cell processing, and the steps provided as obtaining sperm cells, cryopreserving the sperm cells, thawing the sperm cells, processing the sperm cells; and cryopreserving the sorted sperm cells. A further embodiment of the invention is a method of producing a mammal, comprising the method steps of obtaining sperm cells, cryopreserving the sperm cells, thawing the sperm cells, sorting the sperm cells, cryopreserving the sorted sperm cells, thawing the sorted cryopreserved sperm cells, inseminating at least one egg with the sorted cryopreserved sperm cells, fertilizing the at least one egg, and producing a mammal from the at least one fertilized egg.

Furthermore, to achieve the various objects and goals of the invention, the present invention is directed to embodiments providing for artificial insemination (in vivo) and in vitro fertilization procedures. Additionally embodiments may be further directed to the production of mammals or mammalian embryo, and may further be directed to establishing sperm samples such as straws, pellets, or the like, and the processing of semen.

Additional embodiments of the invention are disclosed throughout the description of the invention and in the following claims.

BRIEF DESCRIPTION OF THE DRAWINGS

Each Figure contained in each of the applications set out in Exhibit A are to be considered hereby incorporated by reference as part of this description of the instant invention.

DETAILED DESCRIPTION OF THE PREFERRED EMBODIMENTS

The present invention discloses semen and sperm cell processing and preservation techniques and systems of preservation, stimulation, fertilization, and insemination, addressing one or more sperm cell characteristics or sperm quality, such as sperm cell viability, motility, functionality, stimulation, and preservation, as well as fertility rates, insemination rates, fertilization rates. Further, sperm cell characteristics or sperm quality may be addressed within the context of various processing techniques, such as collection, handling, separation, storage, transportation, usage, fertilization, or insemination techniques.

Sperm cell quality may refer to any one or a combination of the various attributes of sperm cells previously mentioned or further mentioned herein, such as, for example, viability, motility, functionality, stimulation, and preservation of the sperm, or fertility rates, insemination rates, or fertilization rates corresponding to the sperm (such as in the fertility of the sperm). Sperm cell characteristic may refer to any one or a combination of various biological, chemical, physical, physiological, or functional attributes of one or more sperm cells, such as chromosome bearing attributes of the cell, or in some embodiments may refer to sperm cell quality as previously described.

Semen or sperm cell processing techniques may refer to any one or a combination of preservation, stimulation, insemination, fertilization, sorting, selection, separation, or thawing, and may be specifically directed to any one or a combination of collection, handling, selection, storage, transportation, usage, fertilization, or insemination techniques.

Sperm samples may refer to a volume containing sperm cells, potentially including semen, carrier fluid or other materials, and may comprise a pellets, straws, or other known forms of sperm samples.

MAINTAINING OR ENHANCING THE SPERM QUALITY

Sperm cells may be maintained or enhanced in accordance with the present invention, and in some embodiments through sperm processing, such as through sperm cell sorting and preservation, and in accordance with fertilization and insemination techniques. Embodiments may provide preservation of the sperm or sperm cells, or other techniques as may be disclosed in the previously mentioned patent applications and the references listed in the List of References to be Incorporated by Reference, each application and reference expressly incorporated by reference to the extent consistent with the present description, and as further described below.

Sperm cells may also be maintained or enhanced in some embodiments by preservation and stimulation techniques as further described below, and also in further combination with the processing, stimulation, preservation, fertilization, and insemination techniques in the previously mentioned patent applications and the references listed in the List of References to be Incorporated by Reference.

Figure 1:
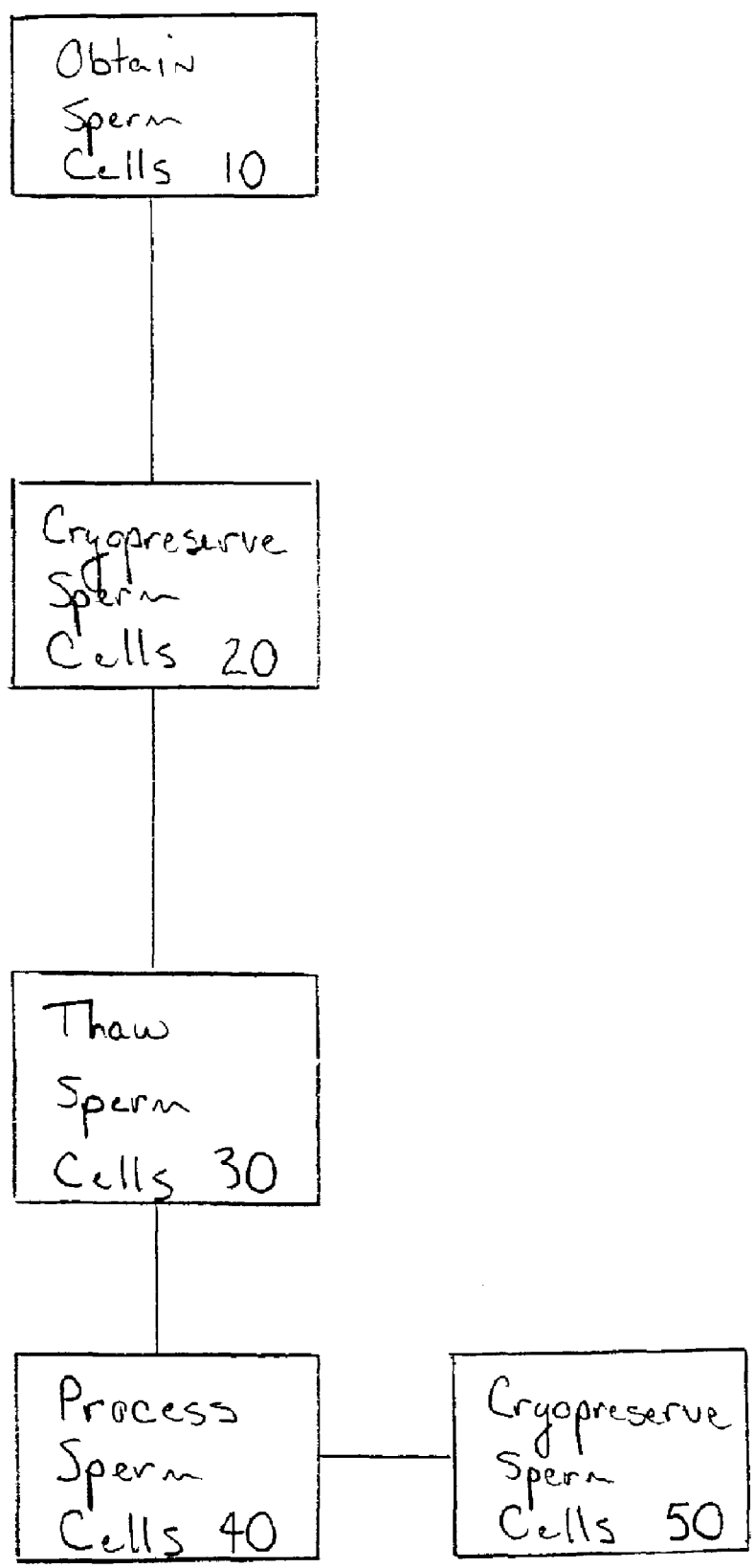
FIG. 1 is a flow diagram for one embodiment of the present invention.

Accordingly, the present invention may provide a method of sperm cell processing. FIG. 1 shows one process for sperm cell processing in accordance with the present invention. As shown, the sperm cells may be obtained 10 from a mammalian source, either directly or in various combinations of steps, such as through a storage facility. The sperm cells may be cryopreserved 20, as further described below. Subsequently, the sperm cells may be thawed 30. Further processing 40, further described below, may then be performed on the sperm cells prior to another cryopreservation of the sperm cells.

Figure 2:
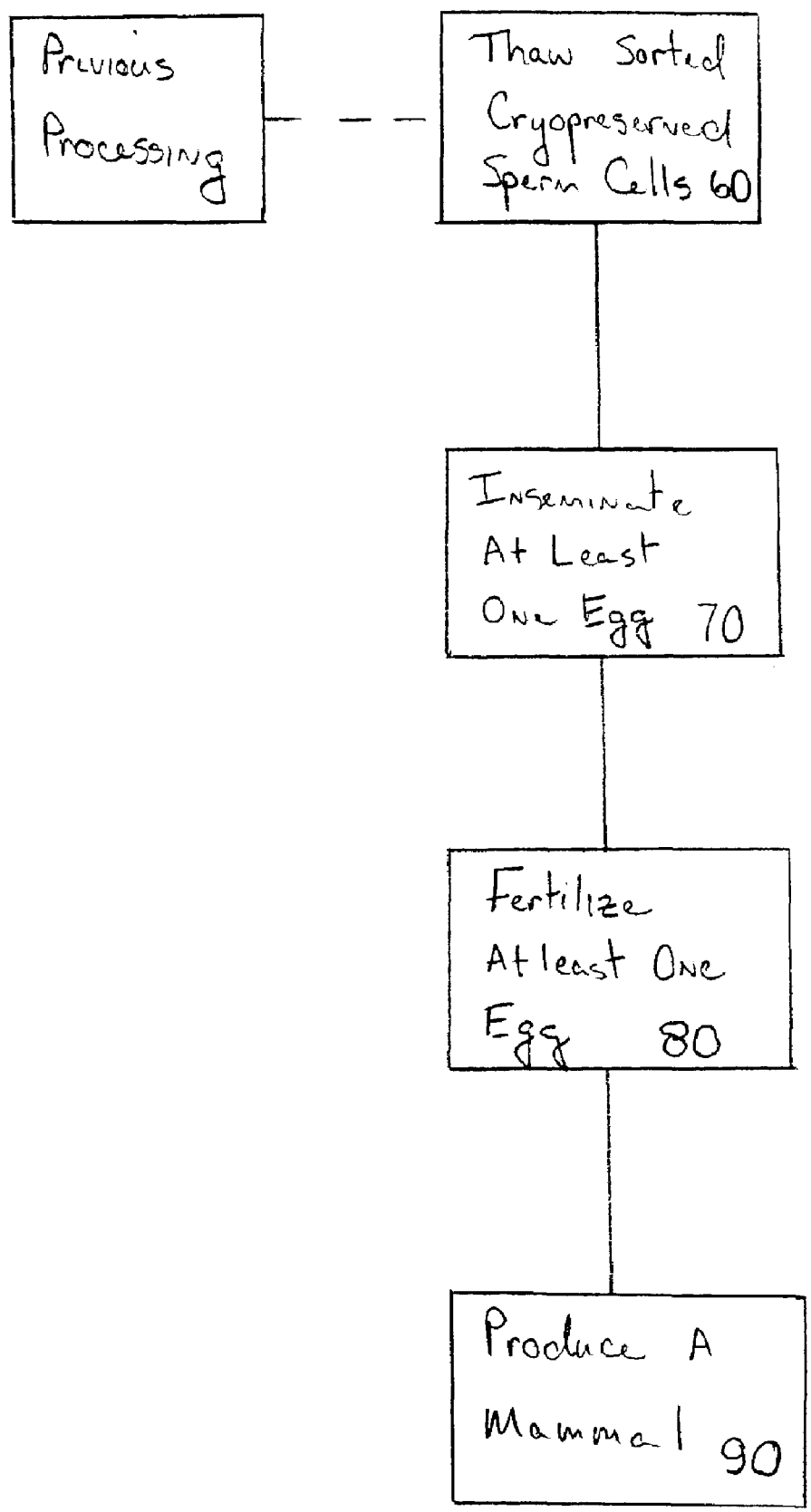
FIG. 2 is a flow diagram for a second embodiment of the present invention, potentially provided in combination with the embodiment of FIG. 1, in some embodiments.

Sperm cell processing, generally, and the process previously described may be conducted for insemination and fertilization. Therefore, an embodiment of the present invention may provide a method of producing a mammal, as shown in FIG. 2. After proceeding with previous processing, or in some embodiments as proceeding with the features 10, 20, 30, 40, and 50, the insemination of the mammal may performed. In one embodiment, the cryopreserved sperm cells may be thawed 60 and the insemination 70 and fertilization 80 of at least one egg with the sperm cells may be conducted. A mammal may then be produced 90 from the egg fertilized by the cryopreserved, processed, cryopreserved, and thawed sperm cells.

Furthermore, embodiments further support in vivo and in vitro techniques. Accordingly, a female of the species of the mammal from which sperm was obtained may be inseminated with the previously processed sperm cells, such as sorted and cryopreserved sperm cells as previously described. At least one egg of the female may then be fertilized and a mammal produced from the at least one fertilized egg. In accordance with in vitro procedures, after insemination and fertilization of at least one egg, a mammalian embryo may be produced, potentially developing into a mammal.

Each of the embodiments previously described may be considered departures from traditional sperm cell processing and the production of mammals and mammalian embryo. It has been traditionally viewed that such processing of sperm cells could not sufficiently ensure sperm quality or provide adequate rates of fertility, insemination, fertilization, or pregnancy. However, and as been taught in the various references cited herein and incorporated by reference, sperm cells may in fact be processed to achieve, for example, the sorting of sperm cells, potentially to differentiate sperm cells as either X chromosome bearing or Y chromosome bearing sperm cells, in some instances to provide for preselection of the sex of a mammal or mammalian embryo. The present invention also provides for such processing, and in some preferred embodiments, additional features of preservation heretofore traditionally thought not to be feasible commercially, or even possible, and heretofore providing a solution to those previously identified but unaddressed issues.

Obtaining Sperm

Semen, and in particular sperm cells, may be obtained and otherwise heretofore processed from mammals in accordance with the present invention such as equids, bovids, felids, ovids, canids, buffalo, oxen, elk, or porcine, or other mammal species. Further, some embodiments may provide obtaining and processing semen or sperm cells from prized mammal species, endangered mammal species, rare individuals of a mammal species, and even from zoological specimens or individuals. The resulting mammal or mammalian embryo may be produced in accordance with the techniques as previously described and as further described below. Sperm samples may be established, in some embodiments, as previously described.

Sample Preservation

Sperm samples are cryopreserved, such as by freezing, using various preservation techniques, such as freezing in a Hepes-buffered crydiluent. Sperm cells may be provided as pellets or straws and may be thawed using various thawing techniques, for example, with ram spermatozoa. Other sperm samples may be provided throughout the processing of sperm cells, and may or may not be cryopreserved when established as a sperm sample or when provided to inseminate or fertilize an egg.

One or more additives, singularly or in combination, may be introduced into the semen, sperm cells, or sperm sample. In one embodiment, a cryodiluent may be introduced into the sperm sample to preserve the sperm cells. The introduction of the additive or additives, such as a cryodiluent, into the sperm sample, and in some embodiments with as a cryopreservation step, potentially referred to as freezing, may maintain or enhance sperm cells, and may further maintain or enhance sperm quality, sperm cell quality, such as sperm cell viability, motility, functionality, stimulation, and fertility rates, and potentially one or more sperm cell characteristics. In other embodiments of the present invention, an additive or additives, such as cryodiluent, singularly or in combination, could be removed from the sperm sample. The removal of the cryodiluent or other additives from the sperm sample, and in some embodiments with cryopreservation steps, may maintain or enhance sperm cells, and may further maintain or enhance sperm quality, such as maintaining or enhancing sperm cell viability, motility, functionality, fertility rates, and potentially one or more sperm cell characteristics.

Sperm Processing

Sperm cells may also be maintained or enhanced in some embodiments of the present invention as part of sperm processing techniques, and sperm quality may further be maintained or enhanced, such as maintaining or enhancing sperm cell viability, motility, functionality, and potentially one or more sperm cell characteristics. Accordingly, in some embodiments, the sperm sample may be preserved, as previously described, such as through cryopreservation, such as freezing, or other preservation techniques such as those disclosed in the previously mentioned patent applications and the references listed in the List of References to be Incorporated by Reference.

Accordingly, cryodiluent or other additives, singularly or in combination, may be introduced into the sperm sample to preserve or stimulate the sperm. In one preferred embodiment, the introduction of the cryodiluent or other additives into the sperm sample contributes to the preservation of the sperm through cryopreservation, freezing the sperm sample, and therefore maintaining or enhancing the sperm cells, and further maintaining or enhancing sperm quality, such as maintaining or enhancing sperm cell viability, motility, functionality, and potentially one or more sperm cell characteristics. As previously mentioned, the cyrodilutent or other additives may be introduced into the sperm sample prior to sample preservation or as sample preservation. The sample may then be processed such as through collection, handling, separation, storage, transportation, usage, fertilization, or insemination techniques as disclosed in the previously mentioned patent applications and the references listed in the List of References to be Incorporated by Reference.

In one embodiment, cryodiluent or other additives, singularly or in combination, may be introduced into a sperm sample previously collected and the sample cryopreserved, such as through freezing, and followed by a thaw of the sample and subsequent processing, including collection, handling, separation, storage, transportation, usage, fertilization, or insemination processing techniques. One such processing step may be provided as sorting, and in some embodiments as the separation of X chromosome bearing sperm cells from Y chromosome bearing sperm cells, potentially into a high purity population sample or samples. Various benefits may be achieved through such a sperm processing technique. For example, various methods of sorting as described in the previously mentioned patent applications achieve a separation of X chromosome bearing sperm cells from Y chromosome bearing sperm cells while minimizing damage to the viable sperm cells. Further, non-viable sperm, contamination, or crydiluent or other additives, for example, may be eliminated through such separation techniques. Additionally, other aspects of sperm quality may be maintained or enhanced, particularly that of sperm cell motility and functionality. The sperm sample may further be stimulated during the processing to maintain or enhance sperm quality as previously described. One such method of sperm processing known in the art is described in U.S. Pat. No. 5,135,759, hereby incorporated by reference in this description, disclosing a flow cytometer sorting technique.

The processing of sperm cells may be performed by sorting the sperm cells as previously described, or in some embodiments, accordance with the following process. Sorting may comprise, in some embodiments, as a selecting of sperm cells based upon at least one desired characteristic, potentially sperm cell quality characteristics, such as viability, motility, functionality, stimulation, and preservation, or one or a combination of various sperm cell characteristics such as biological, chemical, physical, physiological, or functional attributes of one or more sperm cells, such as chromosome bearing attributes of the cell. The sperm cells may be stained, preferably with Hoechst 33342 or like stain or dye, or in combination with such stains or dyes, and the sperms cells differentiated based upon the staining and selection. The cells may then be separated based upon the differentiation and collected. The sperm cells may be so processed in accordance with the various techniques of those references cited herein and expressly incorporated by reference.

EXAMPLE

Preserving and Processing Sample

In one embodiment of a preserving and processing technique, 200 µl of thawed spermatozoa was placed onto a 2ml separation gradient (90%:45%) of PURESPERM™ media, a human preparation, and a Tris based diluent. The gradient preparations were then centrifuged at 1000g for 15 minutes. The post-PURESPERM™ media pellet was removed, slowly diluted 1:4 with warm Tris based diluent and centrifuged at 650g for 3 minutes. The supernatant was removed and the sperm stained, incubated and sorted as previously described. The Tris based diluent was used as the staining medium and ANDROHEP® extender (Minitub, Germany) plus 20% egg yolk was used as the collection medium.

The above example is one of various embodiments of the inventive technique, providing preservation of sperm, such as through cryopreservation or freezing, thawing the sperm, identifying the sperm, such as through staining, and sorting the sperm, such as into X and Y chromosome bearing populations.

Although the previous example provides a sperm preservation technique and processing technique of sperm collection, preservation, thaw and separation, other techniques are encompassed by and explicitly disclosed in the present invention. For example, one or a combination of various collection, handling, separation, storage, transportation, usage, fertilization, or insemination techniques may be performed as part of this present inventive technique. In one embodiment, sperm may be collected, followed by separation of X chromosome bearing sperm cells from Y chromosome bearing sperm cells. A preservation step prior to sperm cell separation may not be needed, for example, during circumstances in which the sorter apparatus is readily available after sperm collection. The sorted sperm sample or samples may then be preserved as an additional step and as previously described, potentially for further handling, separation, storage, transportation, usage, fertilization or insemination. The sorted sperm sample may further be stimulated during the processing to maintain or enhance sperm quality as previously described. The next example describes one example of a processing technique.

EXAMPLE

Processing Samples

Sorted samples were centrifuged at 700 g for 6 min. at room temperature (24C). The supernatant was removed and the sorted sperm could be used "fresh" for AI or in an IVF system; or the remaining pellet was extended 1:4 with the Hepes based cryodiluent, potentially the same diluent used for an original cryopreservation of the sperm, and frozen using various techniques, such as those previously described and as described below. The refrozen and sorted sperm were thawed using methods such as a glass tube shaken in a 37° C. waterbath, and then could be used in an AI or IVF system.

EXAMPLE

Processing Samples

The use of spermatozoa sorted from frozen-thawed pellets in the ovine mammal regarding in vitro fertilization systems. Frozen-sorted and frozen-sorted-frozen sperm used in an ovine IVF system were slowly diluted with 0.5 ml of IVF media, and in some embodiments, using ovine IVF protocol, and centrifuged in a Falcon tube with a tight lid at 300 g for 6 minutes. The supernatant was removed and the remaining sperm quickly placed in the IVF well at a concentration of one million motile sperm/ml. Preferably, a high standard of media preparation (i.e. use of eggs less than 24 hours old, ultracentrifugation of egg yolk diluents and meticulous filtering) and handling of the samples (i.e. constant temperature) is required.

Other preservation, processing, fertilization, and insemination techniques need not include a separation step. For example, the sperm may be collected, followed by a preservation step and subsequent handling, storage, transportation, usage, fertilization, or insemination.

Furthermore, one or more preservation steps may be conducted as part of preservation, processing, fertilization, and insemination techniques, or combinations thereof, such preservation in some embodiments comprising cryopreservation, such as through freezing of the sperm sample, and subsequent steps of thawing, occurring before, concurrent with, or after one or more other processing techniques.

EXAMPLE

Sex-Sorting and Re-Cryopreservation of Frozen-Thawed Ram Sperm for in Vitro Embryo Production Application of sperm sorting to breeding of livestock and wildlife may be limited when the sorter is a long distance from the male(s), as previously described, but would be facilitated by the sorting of cryopreserved and thawed sperm, such as frozen-thawed sperm (Lu KM ex al., Theriogenology 1999:52:1393–1405) and cryopreserving or re-freezing it. High purity sorting with maintained quality of frozen-thawed rain sperm may be achieved after processing to remove the cryodiluent. The aim of this study was to evaluate the functional capacity of frozen-thawed sperm after sorting and a second cryopreservation/thawing step. Frozen semen from 2 rams (n=2 ejaculates per ram) was used throughout. Post-thaw sperm treatments comprised (i) unsorted (Control); (ii) sorted (Frozen-Sort) and (iii) sorted then re-frozen (Frozen-Sort-Frozen). X and Y sperm were separated using a high-speed sorter SX MOFLO® cell sorter, Cytomation, Colo. USA) after incubation with Hoechst 33342 and food dye to eliminate non-viable sperm. Reanalysis revealed high levels of purity for X- and Y-enriched samples for all treatments (87.0+/−4.5%). For IVF, 472 IVM oocytes were inseminated with 1×10(6) motile sperm/mL. After 3 h in SOF medium, oocytes were transferred to Sydney IVF cleavage medium COOK® cleavage medium, QLD, Australia) for 4 d followed by Sydney IVF blastocyst medium COOK® blastocyst medium) for an additional 3 d culture in 5% O2: 5% CO2: 90% N2. Oocytes were assessed for cleavage at 24 and 48 h post-insemination (p.i.). At 52 h p.i., uncleaved oocytes were stained with orcein for assessment of maturation and fertilization. Data from 3 replicates were analyzed by ANOVA, Chi-square and Fisher Exact Test. At insemination, % motile sperm (+/− SEM) was higher (P<0.001) for Frozen-Sort (85.8+/−2.4%) and Frozen-Sort-Frozen (66.7+/−7.7%) than Control (36.7+/−2.1%). Maturation rate was 95.6% (451/472). Cleavage of oocytes in a parthenogenetic control group (no sperm) was low (2/56; 3.6%). Polysperminc fertilization was low (9/451; 2.0%) and did not differ among treatments.

TABLE 1

Fertilization & early embryo development of oocytes after incubation with frozen-thawed unsorted (Control), frozen-thawed & sorted (Froz-Sort) & frozen-thawed, sorted then frozen-thawed (Froz-Sort-Froz) ram sperm. Values in parentheses are percentages.

| Treatment | No. of mature oocytes fertilized[d] | No. of mature oocytes undergoing cleavage after insemination | | No. of cleaved oocytes forming blastocysts | | |
|---|---|---|---|---|---|---|
| | | 24 h | 48 h | Day 5 | Day 6 | Day 7 |
| Control | 40 (67.8) | 26 (44.1) | 36 (61.0) | 4 (11.1) | 13 (36.1) | 16 (44.4)[a] |
| Froz-Sort | 110 (63.6) | 67 (38.7) | 109 (63.0) | 24 (22.1) | 34 (31.2) | 57 (52.3)[ab] |
| Froz-Sort-Froz | 94 (57.7) | 71 (43.6) | 91 (55.8) | 23 (25.3) (64.8)[bc] | 347 (40.7) | 59 |

[d]Monospermic fertilization. Within column, values with different superscripts differ ($P < 0.05$).

Fertilization and cleavage rates were consistently high across treatments. Blastocyst development rate was higher for oocytes fertilized with Froz-Sort-Froz than with Control sperm. These results demonstrate that frozen-thawed ram sperm can be sex-sorted for either immediate or future use in an IVF system after re-cryopreservation.

The above example is one of various embodiments of the inventive technique, providing preservation of sperm, such as through cryopreservation, such as freezing, thawing the sperm, sorting the sperm, such as into X and Y chromosome bearing populations, preserving the sorted sample, such as through cryopreservation or freezing, and further including thawing the sperm sample for use, such as for fertilization or insemination.

Consideration should be given to fertility rates respective of preservation and processing procedures, such as separation for sex-sorting and cryopreservation of sperm samples, as the next Example describes, and in combination with cryopreservation, thawing, processing, and subsequent cryopreservation, as disclosed in this description.

EXAMPLE

Effect of Dose of Sperm Processed for Sex-Sorting and Crypreservation on Fertility in Ewes Lambs have been produced after artificial insemination (AI) with low numbers ($2-4 \times 10^6$) of cryopreserved sex-sorted sperm. Fewer ewes were pregnant after AI with X- or Y-sorted frozen-thawed (25%, 15% respectively) than with a commercial dose of unsorted frozen-thawed sperm (54%). The object of the present study was to determine the minimum numbers of sorted frozen-thawed sperm required to obtain pregnancy rates similar to those obtained with unsorted sperm.

A sample of sperm from single ejaculates of 2 rams was stained, incubated, analyzed and sorted using a modified high speed cell sorter (MOFLO® cell sorter Cytomation, Fort Collins, Colo. USA) as previously described. Sperm were processed at 15,000–18,000/serc without sex-sorting into 10 ml centrifuge tubes pre-soaked with 1% BSA in sheath fluid containing 0.2 ml Tris-buffered medium and 20% egg yolk (v/v). For every sample, $1.3 \times 10^6$ sperm were sex-sorted and analyzed to determine purity. Sorted and unsorted (control) samples were extended with a zwitterions-buffered diluent containing 13.5% egg yolk and 6% glycerol and frozen as 250ul pellets containing $5 \times 10^6$ sperm. The time of estrus was controlled in 144 Merino ewes by progestagen sponges (FGA, Vetrepharm A/Asia, Sydney) inserted intravaginally for 12 days and an injection of 400 I.U of PMSG (Pregnecol, Vetrepharm A/Asia) at sponge removal (SR). Thirty-six h after SR 134 ewes were injected with 40 µg GnRH (FERTAGYL® GnRH, Intervet) to control the time of ovulation. One hundred and eleven ewes were inseminated in the uterus by laparoscopy 57–60 h after SR with 5, 10, 20 or $40 \times 10^6$ sorted or unsorted frozen-thawed sperm. Thirteen ewes not given GnRH were inseminated with a commercial dose of unsorted frozen-thawed sperm. Thirteen ewes not given GnRH were inseminated with a commercial dose of unsorted frozen-thawed sperm 57–58 h after SR. Pregnancy was diagnosed by ultrasound on d53. The data were analyzed by Chi-square.

Sperm motility after thawing was 37.8+/−1.78% (sorted) and 42.9+/−0.93% (unsorted). Seven of 13 (53.8%) ewes not given GnRH were pregnant. Of the GnRH-treated ewes the proportion pregnant was affected by the number of sperm inseminated ($p<0.05$) but not by ram or type of sperm ($p>0.05$). For ewes inseminated with sorted or unsorted (control) frozen-thawed sperm, pregnancy rate was higher for inseminates of 10 and $40 \times 10^6$ than for 5 and $20 \times 10^6$ sperm (Table 2). The results suggest that a minimum of $40 \times 10^6$ sorted frozen-thawed sperm inseminated close to the time of ovulation are required to obtain commercially acceptable pregnancy rates.

TABLE 1

Pregnancy after intrauterine insemination of ewes with frozen-thawed control and sorted ram sperm.

| Dose (x$10^6$ sperm) | No. ewes inseminated | No. ewes pregnant | % ewes pregnant |
|---|---|---|---|
| 5 | 30 | 10 | 33.3[a] |
| 10 | 28 | 16 | 57.1[b] |
| 20 | 29 | 10 | 34.5[a] |
| 40 | 23 | 16 | 69.6[a] |

[ab]Within columns different superscripts differ ($p < 0.05$).
[a]This research was supported by XY, Inc; CO, USA; The Australian Research Council, Vetrephann A/Asia.

The invention can further include a sperm sample, such as a straw, and in some embodiments straws utilized in IVF, produced in accordance with any of the above described embodiments of the invention, such as any of the processing, stimulation, preservation, fertilization, and insemination techniques, and be of maintained or enhanced sperm quality, such as a straw of desired viability, motility, functionality, or other characteristics, or combinations of characteristics, potentially resulting in desirable levels of fertility rates, and in some embodiments, particularly for equine mammals.

The sperm sample or straw may be particularly suited for individual production embryos.

The invention can further include a mammal produced in accordance with any of the above described embodiments of the invention, or can include a mammal of predetermined sex in accordance with the various embodiments of the invention that provide sperm cell insemination samples having an enriched population of either X-chromosome bearing sperm cells or enriched population of Y-chromosome bearing sperm cells, or a mammal produced in accordance with any embodiment of the invention in which a sperm cell insemination sample containing a low number of sperm cells compared to the typical number used to inseminate that particular species of mammal is used, or elk progeny produced in accordance with the invention as described above.

The invention further includes various processing, preservation, stimulation, fertilization, and insemination techniques as disclosed herein and as disclosed in the previously mentioned patent applications and references. Accordingly, the various semen and sperm cell processing systems and systems of preservation, stimulation, fertilization, and insemination, embodiments, in various embodiments addressing sperm quality such as one or more sperm cell characteristics, such as viability, motility, functionality, or fertilization rates consistent with the disclosures of the previously mentioned patent applications and references. Further, sperm cell characteristics may be addressed within the context of various collection, handling, separation, storage, transportation, usage, fertilization, or insemination techniques, and in those or other various embodiments, within the context of assaying, testing, or determining the biological, chemical, physical, physiological, or functional attributes of sperm cells. Therefore, systems of the present invention may provide sperm cell processing, stimulation, preservation, fertilization, and insemination, for example, incorporating flow sorting techniques, high purity separation techniques, low dose fertilization and insemination techniques, heterospermic insemination procedures, such as to assess comparative viability, motility, function, or fertility processed in various pressure environments within a sorter, as but a few examples.

The disclosure incorporated by reference, such as the various examples provided of separating X chromosome bearing sperm cells from Y chromosome bearing sperm cells, and other disclosed techniques of collection, handling, separation, storage, transportation, usage, fertilization, and insemination are not meant to limit the present invention to any particular embodiment, whether apparatus, method, or otherwise. The descriptions incorporated by reference and the various examples should not be construed to limit the present invention to only techniques for sperm sorting or only techniques for sperm preservation. This disclosure, however, may be understood to incorporate the various techniques in the context of the various embodiments of the present invention. Further, the present invention should be considered to incorporate such techniques of sperm processing, preservation, stimulation, fertilization, and insemination consistent with the features disclosed.

As can be easily understood from the foregoing, the basic concepts of the present invention may be embodied in a variety of ways. It involves both a sperm cell process system including both techniques as well as devices to accomplish sperm cell processing. In this application, various sperm cell processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood as encompassed by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered as encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "cryopreserver" should be understood to encompass disclosure of the act of "cryopreserving"—whether explicitly discussed or not—and, conversely, were there effectively disclosure of the act of "cryopreserving", such a disclosure should be understood to encompass disclosure of a "cryopreserver" and even a "means for cryopreserving." Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing methods as herein disclosed and described, ii) the related systems, devices, and multiple apparatus disclosed and described, iii) similar, equivalent, and even implicit variations of each of these systems and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented.

The Applicant may have presented claims with an set of initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

What is claimed is:

1. A method of sperm cell processing, comprising the steps of:
    obtaining sperm cells from a male of a mammalian species;
    cryopreserving said obtained sperm cells;
    thawing said cryopreserved sperm cells;
    sorting said thawed sperm cells into X chromosome-bearing sperm cells and Y chromosome-bearing sperm cells; and
    cryopreserving said sorted sperm cells to yield twice-cryopreserved sorted sperm cells;
    wherein an increased percentage of said twice-cryopreserved sorted sperm cells, when thawed, are motile, compared to said thawed sperm cells, and
    wherein said twice-cryopreserved sorted sperm cells, when thawed, yield blastocysts at an increased rate, compared to said thawed sperm cells, when used to fertilize eggs from a female of said mammalian species.

2. A method of sperm cell processing as described in claim 1 wherein said step of sorting comprises selecting said sperm cells based upon at least one desired sperm cell characteristic.

3. A method of sperm cell processing as described in claim 2 wherein said step of selecting comprises staining said sperm cells based upon at least one desired sperm cell characteristic.

4. A method of sperm cell processing as described claim 3 wherein said step of selecting further comprises separating said sperm cells having said at least one desired sperm cell characteristic.

5. A method of sperm cell processing as described in claim 4 further comprising the step of collecting said sperm cells.

6. A method of sperm cell processing as described in claim 1 wherein said step of sorting comprises flow cytometer sorting.

7. A method of sperm cell processing as described in claim 1 further comprising the step of establishing a sperm sample from said sorted sperm cells and wherein said step of cryopreserving said sorted sperm cells comprises cryopreserving said sperm sample.

8. A method of sperm cell processing as described in claim 7 wherein said step of establishing a sperm sample comprises establishing a plurality of sperm samples and wherein said step of cryopreserving said sorted sperm cells comprises cryopreserving said plurality of samples.

9. A method of sperm cell processing as described in claim 1 further comprising the step of thawing said twice-cryopreserved sorted sperm cells.

10. A method of sperm cell processing as described in claim 9 further comprising the step of establishing a sperm sample from said twice-cryopreserved sorted thawed sperm cells.

11. A method of sperm cell processing as described in claim 10 wherein said step of establishing a sperm sample from said twice-cryopreserved sorted thawed sperm cells comprises establishing a plurality of sperm samples from said twice-cryopreserved sorted thawed sperm cells.

12. A method of sperm cell processing as described in claim 1 wherein said step of obtaining comprises obtaining semen, wherein said step of cryopreserving comprises cryopreserving said semen, and wherein said step of thawing comprises thawing said cryopreserved semen.

13. A method of sperm cell processing as described in claim 1 wherein said step of obtaining comprises obtaining sperm cells from zoological specimens.

14. A method of sperm cell processing as described in claim 1, wherein at least about 83.4% of said twice-cryopreserved sorted sperm cells are motile.

* * * * *

UNITED STATES PATENT AND TRADEMARK OFFICE
CERTIFICATE OF CORRECTION

PATENT NO. : 7,169,548 B2
APPLICATION NO. : 10/340881
DATED : January 30, 2007
INVENTOR(S) : William M. C. Maxwell et al.

Page 1 of 1

It is certified that error appears in the above-identified patent and that said Letters Patent is hereby corrected as shown below:

In the Specification,

Column 10, line 35, "(Lu KM ex al., The-" should read -- (Lu KH, et al., The- --

Column 10, line 38, "frozen-thawed rain sperm" should read -- frozen thawed ram sperm --

Column 11, Table 1, line 14, row Froz-Sort-Froz, under Column Day 7, "59" should read -- 59 $(64.8)^{bc}$ --

Column 11, Table 1, line 15, row Froz-Sort-Froz, under Column Day 5, "$(64.8)^{bc}$" should be deleted Column 12, line 45, "Table 1" should read -- Table 2 --

Signed and Sealed this
Sixteenth Day of December, 2014

Michelle K. Lee
*Deputy Director of the United States Patent and Trademark Office*